United States Patent
Canós et al.

(10) Patent No.: US 7,439,411 B2
(45) Date of Patent: Oct. 21, 2008

(54) ZEOLITE CATALYST FOR THE ALKYLATION OF AROMATIC COMPOUNDS WITH OLEFINS, ALCOHOLS OR POLYALKYLATED AROMATIC COMPOUNDS

(75) Inventors: Avelino Corma Canós, Valencia (ES); Fernando Rey García, Valencia (ES); María José Díaz Cabañas, Valencia (ES)

(73) Assignees: Consejo Superior de Investigaciones Cientificas, Madrid (ES); Universidad Politecnica de Valencia, Valencia (ES)

( * ) Notice: Subject to any disclaimer, the term of this patent is extended or adjusted under 35 U.S.C. 154(b) by 765 days.

(21) Appl. No.: 11/033,047

(22) Filed: Jan. 11, 2005

(65) Prior Publication Data

US 2005/0192469 A1    Sep. 1, 2005

Related U.S. Application Data

(63) Continuation of application No. PCT/ES03/00351, filed on Jul. 10, 2003.

(30) Foreign Application Priority Data

Jul. 11, 2002  (ES)  ................................ 200201677

(51) Int. Cl.
*C07C 2/66* (2006.01)
(52) U.S. Cl. ....................................................... 585/467
(58) Field of Classification Search .................. 585/467
See application file for complete search history.

(56) References Cited

U.S. PATENT DOCUMENTS

| 4,292,457 A | 9/1981 | Klotz |
| 4,891,458 A | 1/1990 | Innes et al. |
| 5,030,785 A | 7/1991 | Huss, Jr. et al. |

FOREIGN PATENT DOCUMENTS

| ES | 2 192 935 | 5/2001 |
| ES | 2 195 744 | 10/2001 |

*Primary Examiner*—Thuan Dinh Dang
(74) *Attorney, Agent, or Firm*—Klauber & Jackson LLP

(57) ABSTRACT

The invention relates to a method of preparing an alkylated aromatic compound. The inventive method is characterized in that it comprises an alkylation reaction of an aromatic compound with an alkylating agent which is selected from an olefin, an alcohol and a polyalkylated aromatic compound, in the presence of a catalyst which is a porous crystalline material with the following chemical composition in the calcined form: $X_2O_3:nYO_2:m\,ZO_2$, wherein (n+m) is at least 5, X is at least a trivalent element, Z is Ge, Y is at least a tetravalent element different from Ge and the n/m ratio is at least 1. Said method is particularly suitable for obtaining cumene.

16 Claims, No Drawings

ZEOLITE CATALYST FOR THE ALKYLATION OF AROMATIC COMPOUNDS WITH OLEFINS, ALCOHOLS OR POLYALKYLATED AROMATIC COMPOUNDS

This application is a continuation of the international application number PCT/ES03/000351, filed Jul. 10, 2003.

TECHNICAL FIELD

The present invention relates to the field of heterogeneous catalysis.

BACKGROUND

Cumene is a product of commercial interest that is used as raw material in the production of phenol and acetone. Numerous processes have been developed using acid catalysts. A general reference on the catalysts and processes used can be found in "Encyclopedia of Chemical Processing and Design", J. J. McKezta and W. A. Cunningham Editors, V. 14, pp. 33-55 (1982). The alkylation of benzene with propylene, in addition to seeking a high conversion of propylene and a high selectivity for the monoalkylated product, isopropylbenzene (cumene), requires a minimum amount of n-propylbenzene (NPB) be formed. This is because NPB interferes with the oxidation of cumene to produce phenol and acetone, and consequently there is a need for a stream of cumene with the least amount of NPB impurities possible. Since it is difficult to separate cumene from NPB by conventional methods, such as distillation for example, then, logically, the yield of NPB must be as low as, possible, and at any rate very low, during the alkylation or benzene with propylene.

From the viewpoint of the catalysts used in this process, acids such as $H_3PO_4$, $AlCl_3$ and HCl have conventionally been used, although they do give' rise to problems arising from corrosion and loss of selectivity owing to the formation of polyalkylated products. Zeolites have also been used as catalysts for the alkylation of aromatics; thus, for example, patent U.S. Pat. No. 4,292,457 describes zeolite ZSM-5 as a catalyst for the alkylation of benzene with propylene.

However, probably owing to the small diameter of its channels, this zeolite proves to be not very selective for the desired process. There are also many patents that describe the use of Faujasite and modified Faujasites as catalysts for the production of cumene by alkylation of benzene with propylene. More specifically, zeolite Y has good activity at temperatures of between 130 and 180° C., with good selectivity for the desired products. However, this selectivity decreases sharply when the conversion of benzene is increased, and it is therefore necessary to work with high benzene/propylene ratios in the feed. This results in high benzene recycling costs. Zeolite Beta has also been claimed as a catalyst for the alkylation of benzene with propylene in various patents, such as U.S. Pat. No. 4,891,458, U.S. Pat. No. 5,030,786, EP 432 814, EP 439 632, and EP 629 599. This zeolite produces good results in terms of activity and selectivity, but its performance can be improved as regards both selectivity for NPR and the stability of the catalyst.

Spanish patent application P200101145 describes a zeolite material called ITQ-21. However, it does not disclose a process for the alkylation of aromatic products with olefins and alcohols or polyalkylated aromatics in which this zeolite is used as catalyst. Spanish application P20012287, also, relates to said crystalline solid material, specifically to its use in cracking, but it does not describe an alkylation process according to the present invention.

The subject of the present invention is a process for the alkylation of aromatic products with olefins and alcohols or polyalkylated aromatics in the presence of a catalyst with an X-ray pattern and a chemical composition corresponding to ITQ-21, this catalyst being not only active but also, in the case of cumene, producing a very low yield of n-propylbenzene, an unwanted product.

DESCRIPTION OF THE INVENTION

The present invention relates to a process for preparing an alkylated aromatic compound, which process comprises an alkylation reaction of an aromatic compound with an alkylating agent which is selected from an olefin, an alcohol and a polyalkylated aromatic compound, in the presence of a catalyst which is a porous crystalline material with a chemical composition as expressed in its calcined form as:

$X_2O_3 : nYO_2 : mZO_2$ in which
(n+m) is at least 5,
X is a trivalent element,
Z is Ge,
Y is at least one tetravalent element other than Ge, and the n/m ratio is at least 1,
said material having, in its calcined form, an X-ray diffraction pattern whose most characteristic diffraction peaks are:

TABLE 1

| d(±0.3 Å) | Relative Intensity |
|---|---|
| 13.64 | vs |
| 7.87 | vs |
| 4.82 | w |
| 4.55 | m |
| 4.11 | m |
| 3.41 | m | in which d represents the interplanar spacing in angstrom and the relative intensity of the lines is calculated as a percentage of the most intense peak, with
vs being a very strong relative intensity of 80-100,
m being a medium relative intensity of 40-60, and
w being a weak intensity of 20-40.

The trivalent elements incorporated are preferably Al, B, G, Fe, or mixtures thereof and the tetravalent elements are, for example, Si, Ge, Ti, or mixtures thereof, preferably Si and/or Ge.

The catalyst used in the alkylation process of the present invention can be prepared by hydrothermal synthesis from a mixture containing a source of one or more tetravalent elements, for example tetraethyl orthosilicate, amorphous silica, or silica with a mesoporous structure with or without long-range order (non-limiting examples) in the case of Si, or in the case of Ge the source can be germanium oxide, etc., optionally a source of one or more trivalent elements, for example aluminum alkoxides, alumina or metal aluminum (non-limiting examples) in the case where said trivalent element is Al, an organic structure directing agent (OSDA), water, and, in some cases, a source of fluoride ions, such as HF or $NH_4F$, among others. As structure directing agent a salt with an N(16)-methylsparteinium cation or the corresponding hydroxide can be used.

The reaction mixture has the following composition in terms of oxide molar ratios:

|  | Molar Ratio | |
| --- | --- | --- |
| Reagents | Useable | Preferred |
| $(YO_2 + ZO_2)/X_2O_3$ | greater than 5 | greater than 7 |
| $H_2O/(YO_2 + ZO_2)$ | 1-50 | 2-20 |
| $R/(YO_2 + ZO_2)$ | 0.1-3.0 | 0.1-1.0 |
| $YO_2/ZO_2$ | greater than 1 | greater than 5 |

If fluoride anions are used, the ratio of this component in the synthesis mixture is as follows:

|  | Preferred | Useable |
| --- | --- | --- |
| $F/(YO_2 + ZO2)$ | 0.1-3.0 | 0.1-1.0 |

The resulting mixture is placed in a steel autoclave with a Teflon lining and is heated at the desired temperature (between 80 and 200° C.) for a time of between 12 hours and 30 days. The contents of the autoclave are filtered, washed and dried. The organic material in the solid obtained is removed by methods known in the literature, such as: calcination in the presence of $N_2$ followed by calcination in air, direct calcination in air, extraction of the organic material with inorganic or organic acids or by a treatment with ozone. The resulting material has an X-ray diffraction pattern in which at least the lines printed out in Table 1 are present.

The resulting catalyst is pelletized according to methods well known in the literature, using a diluent such as $SiO_2$, $Al_2O_3$, a clay, zirconia, magnesium oxide, or a mixture thereof, in zeolite/diluent proportions of between 20 and 95%, preferably between 40 and 0% by weight.

The catalyst can be treated with an aqueous solution of an inorganic acid, such as $HNO_3$, $H_2SO_4$, $H_3PO_4$ or $HClO_4$, at a pH of between 0 and 1.5, at temperatures of between 20 and 100° C., for a time of between 10 and 400 minutes, depending on the acid concentrations and the treatment temperature. The ratio of the catalyst to the acid aqueous solution is between 0.05 and 1, and preferably between 0.1 and 0.5 by weight.

Once calcined at a temperature of between 450 and 700° C., the resulting catalyst, with or without acid treatment, but containing acid centers, is used as catalyst in the alkylation of aromatics with olefins, alcohols or polyalkylated products, and more specifically in the alkylation of benzene with propylene.

In an alternate embodiment, the zeolite material in uncalcined form, or following heat treatment, can undergo balancing cation exchange, if said cations are present, in which said balancing cations are exchanged with other balancing cations such as metal ions, $H^+$ and $H^+$ precursors, such as $NH^+_4$ for example. Among the cations that can be introduced by ion exchange, preference is given to those that can play a positive role in the activity of the material as a catalyst, more specifically cations such as $H^+$, cations of rare earths and Group VIII metals, and metals of Groups IIA, IIIA, IVA, VA, IB, IIB, IIIB, IVB, VB, VIIB of the Periodic Table of the Elements. As examples of these cations, mention may be made of cations with an n+ charge, selected from among $Na^+$, $K^+$, $Cs^+$, $Ca^{2+}$, $Mg^{2+}$, $Cu^{2+}$ and $Co^{2+}$.

According to the aromatics alkylation process of the present invention, the alkylation reaction takes place at a reaction temperature of between 60 and 350° C., preferably between 80 and 300° C. The pressure is between 1.4 and 7.0 MPa, preferably between 1.4 and 4.1 MPa. The space velocity (WHSV) of the reagents is between 0.2 and 10 hours$^{-1}$, preferably between 0.5 and 10 hours$^{-1}$. The aromatic compound/alkylating agent molar ratio is between 2 and 20, preferably between 2 and 15.

In a particularly preferred embodiment of the process of the present invention, the alkylated aromatic compound is cumene, the aromatic compound is benzene and the alkylating agent is propylene.

The alkylation reaction for this preferred embodiment takes place at a reaction temperature of between 60 and 350° C., preferably between 80 and 300° C. The pressure is between 1.4 and 7.0 MPa, preferably between 1.4 and 4.1 MPa, the space velocity (WHSV) of reagents is between 0.2 and 10 hours$^{-1}$, preferably between 0.5 and 10 hours$^{-1}$, and the benzene/propylene molar ratio is between 2 and 20, preferably between 2 and 15.

According to an alternate embodiment of the present process, an olefin is reacted with an aromatic compound under alkylation conditions, in which a liquid phase at least partially exists, in a molar ratio of between 2 and 20, in the presence of the catalyst.

According to this embodiment, the olefin preferably comprises 2 to 20 carbon atoms.

According to the process of the present invention, the aromatic compound is preferably selected from the group formed by benzene, naphthalene, anthracene, phenanthrene, and substituted derivatives thereof, and, more preferably still, the aromatic compound is benzene.

Among the substituted derivatives of benzene, naphthalene, anthracene and phenanthrene, preference is given to the aromatic compounds selected from among alkylbenzene, hydroxybenzene, alkoxybenzene, alkylnaphthalene, hydroxynaphthalene, alkoxynaphthalene, alkylanthracene, hydroxyanthracene, alkoxyanthracene, alkylphenanthrene, hydroxyphenanthrene, and alkoxyphenanthrene.

An additional alternate embodiment of the present invention relates to an alkylation process as defined above, in which the alkylating agent is a polyalkylated aromatic compound, the aromatic compound is a non-alkylated aromatic compound, and in which, during the alkylation, at least one alkyl group is transferred from the polyalkylated aromatic compound to the non-alkylated aromatic compound.

According to this alternate embodiment, the polyalkylated aromatic compound is preferably a compound comprising an alkyl group having 2-20 carbon atons, and more preferably still said alkyl group has 6-20 carbon atoms.

Also according to this alternate embodiment, the aromatic compound is preferably selected from the group formed by benzene, naphthalene, anthracene, phenanthrene, and substituted derivatives thereof, and, more preferably still, it is benzene. Among the substituted derivatives of benzene, naphthalene, anthracene and phenanthrene, preference is given to the aromatic compounds selected from among alkylbenzene, hydroxybenzene, alkoxybenzene, alkylnaphthalene, hydroxynaphthalene, alkoxynaphthalene, alkylanthracene, hydroxyanthracene, alkoxyanthracene, alkylphenanthrene, hydroxyphenanthrene, and alkoxyphenanthrene. Also preferably, the polyalkylated aromatic compound is a polyisopropylbenzene and the non-alkylated aromatic compound is benzene.

According to this invention—the acid catalysts prepared with the crystalline structure described—it has been found that, when applied in acid form to the alkylation of aromatics with olefins, alcohols or polyalkylated aromatic compounds, and more specifically when used in the alkylation of benzene with propylene, they are very active and have a surprisingly low selectivity for the production of NPB. Furthermore, the selectivity for cumene can be increased by introducing appropriate amounts of alkali metals, alkaline earth metals, or metal cations into the material, by ion exchange, as stated above. Its selectivity can also be increased by removing the surface acidity by extraction of trivalent cations in the network, such as Al and/or B for example, by means of a treatment with inorganic acids or other chemical agents that are capable of extracting said elements. Catalysts based on the cationic exchange or leaching treatments mentioned above make it possible to decrease selectivity for polyalkylated products.

The catalysts thus obtained and formulated with the diluents and proportions described above are used in the reaction systems and conditions described above for the alkylation of aromatics with olefins, alcohols, or polyalkylated aromatic compounds, and more specifically, the alkylation of benzene with propylene.

A number of illustrative examples of the preparation of the catalyst and its use in the alkylation of aromatics with olefins and alcohols are described below, illustrated by means of alkylation of benzene with propylene.

EXAMPLES

Example 1

This example illustrates the preparation of an acidic crystalline solid catalyst.

0.86 g of aluminum isopropoxide and 0.53 g of $GeO_2$ were dissolved in 34.42 g of N(16)-methylsparteinium hydroxide solution at a concentration of 1.53 mol/kg. 4.74 g of tetraethyl orthosilicate were hydrolyzed in the solution obtained, and stirring was maintained, allowing all the alcohol formed during hydrolysis to evaporate. 0.52 g of hydrofluoric acid solution (48.1% HF by weight) was then added. The final composition of the synthesis gel was:

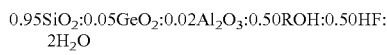

0.95$SiO_2$:0.05$GeO_2$:0.02$Al_2O_3$:0.50ROH:0.50HF: 2$H_2O$ in which ROH is N(16)-methylsparteinium hydroxide.

The gel was heated at 175° C. for 5 days in steel autoclaves with a Teflon internal lining. The solid obtained was filtered, washed with distilled water, dried at 100° C. and calcined in air at 580° C. for 3 hours. The X-ray diffraction diagram for this material presents the peaks shown in Table 2.

TABLE 2

| d(±0.2) (Å) | Relative Intensity |
|---|---|
| 13.64 | vs |
| 9.64 | vw |
| 7.87 | vs |
| 6.82 | vw |
| 4.82 | w |
| 4.55 | m |
| 4.11 | m |
| 3.78 | vw |
| 3.41 | m |
| 3.31 | vw |
| 3.13 | vw |
| 3.05 | vw |
| 2.91 | vw |
| 2.67 | vw |
| 2.62 | vw |

TABLE 2-continued

| d(±0.2) (Å) | Relative Intensity |
|---|---|
| 2.53 | vw |
| 2.41 | vw |

Example 2

This example illustrates the preparation of the catalyst in basic medium.

0.25 g of aluminum isopropoxide and 0.53 g of $GeO_2$ were dissolved in 26.58 g of N(16)-methylsparteinium hydroxide solution at a concentration of 0.56 mol/kg. 5.21 g of tetraethyl orthosilicate were hydrolyzed in the solution obtained, and stirring was maintained, allowing evaporation of all the alcohol formed during hydrolysis and of the water necessary until the final composition of the gel was:

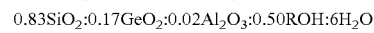

0.83$SiO_2$:0.17$GeO_2$:0.02$Al_2O_3$:0.50ROH:6$H_2O$ in which ROH is N(16)-methylsparteinium hydroxide.

The gel was heated at 175° C. for 20 days in steel autoclaves with a Teflon internal lining. The solid obtained was filtered, washed with distilled water, dried at 100° C. and calcined in air at 580° C. for 3 hours. The X-ray diffraction diagram for this material presents the peaks shown in Table 2.

Example 3

The present example illustrates the use of a material prepared according to Example 1 as a catalyst in the alkylation of benzene with propylene.

A sample with an Si/Al ratio of 25, prepared according to Example 1, was pelletized, selecting a particle size between 0.25 and 0.42 mm to perform the reaction. The zeolite (0.55 g) was diluted with silicon carbide (0.59-0.84 mm) in an SiC/zeolite weight ratio of 5. The diluted catalyst was placed in a tubular steel reactor 1 cm in diameter, and 100 ml/min were passed through under standard $N_2$ conditions at 150° C. for 1.5 hours. The temperature was then lowered to 20° C. and the flow of $N_2$ was stopped. At this point, benzene (1200 μl/min) was fed in and the pressure was raised to 3.5 MPa. When the pressure of 3.5 MPa was reached, the temperature was raised to 125° C. and the feed of propylene (270 μl/min) was begun, at a benzene/propylene molar ratio of 3.4.

The results in terms of converted propylene are shown in Table 3.

TABLE 3

Conversion and selectivity in the alkylation of benzene with propylene at 125° C., B/P = 3.4 mol/mol, prop WHSV = 18 $h^{-1}$, P = 3.5 MPa, Si/Al ratio = 25

| Reaction time (min) | Conversion (%) | Selectivity with respect to propylene (%) | | | |
|---|---|---|---|---|---|
| | | Cumene | DIPB | NPB | Other |
| 15 | 99.39 | 87.61 | 11.86 | 0.04 | 0.49 |
| 120 | 99.88 | 88.29 | 11.12 | 0.03 | 0.56 |
| 195 | 99.14 | 87.81 | 11.29 | 0.03 | 0.87 |
| 270 | 99.30 | 87.76 | 11.40 | 0.04 | 0.80 |

In this example, the NPB and diisopropylbenzene (DIPS) values are very low, lower than those obtained with a zeolite Beta with the same Si/Al ratio operating under the same reaction conditions.

Example 4

The present example shows the influence of the space velocity (WHSV) (12 h$^{-1}$) on the conversion and selectivity for the alkylation of benzene with propylene using the same catalyst as in Example 3, the rest of the reaction conditions being the same as in Example 3.

The conversion results and reaction time are shown in Table 4.

TABLE 4

Conversion and selectivity in the alkylation of benzene with propylene at 125° C., B/P = 3.4 mol/mol, prop WHSV = 12 h$^{-1}$, P = 3.5 MPa, Si/Al ratio = 25

| Reaction time (min) | Conversion (%) | Selectivity with respect to propylene (%) | | | |
|---|---|---|---|---|---|
| | | Cumene | DIPB | NPB | Other |
| 90 | 99.16 | 81.65 | 16.47 | 0.02 | 0.32 |
| 225 | 98.70 | 86.96 | 12.16 | 0.02 | 0.86 |
| 345 | 98.20 | 85.42 | 13.70 | 0.03 | 0.84 |

The invention claimed is:

1. A process for preparing an alkylated aromatic compound, which process comprises an alkylation reaction of an aromatic compound with an alkylating agent which is selected from an olefin, an alcohol and a polyalkylated aromatic compound, in the presence of a catalyst which is a porous crystalline material with a chemical composition expressed in its calcined form as: $X_2O_3:nYO_2:mZO_2$ in which (n+m) is at least 5, X is a trivalent element, Z is Ge, Y is at least one tetravalent element other than Ge, and the n/m ratio is at least 1, said material having, in its calcined form, an X-ray diffraction pattern whose most characteristic diffraction peaks are:

TABLE 1

| d(±0.3 Å) | Relative Intensity |
|---|---|
| 13.64 | vs |
| 7.87 | vs |
| 4.82 | w |
| 4.55 | m |
| 4.11 | m |
| 3.41 | m | in which d represents the interplanar spacing in Ångstrom and the relative intensity of the lines is calculated as a percentage of the most intense peak, with vs being a very strong relative intensity of 80-100, m being a medium relative intensity of 40-60, and w being a weak intensity of 20-40.

2. The process as claimed in claim 1, wherein the alkylation reaction takes place at a reaction temperature of between 60 and 350° C., the pressure is between 1.4 and 7.0 MPa, the space velocity (WHSV) of reagents is between 0.2 and 10 hours$^{-1}$, and the aromatic compound/alkylating agent molar ratio is between 2 and 20.

3. The process as claimed in claim 1, wherein the alkylated aromatic compound is cumene, the aromatic compound is benzene and the alkylating agent is propylene.

4. The process as claimed in claim 3, wherein the alkylation reaction takes place at a reaction temperature of between 60 and 350° C., the pressure is between 1.4 and 7.0 MPa, the space velocity (WHSV) of reagents is between 0.2 and 10 hours.sup.−1, and the benzene/propylene molar ratio is between 2 and 20.

5. The process as claimed in claim 1, wherein an olefin is reacted with an aromatic compound under alkylation conditions, in which a liquid phase at least partially exists, in a molar ratio of between 2 and 20, in the presence of the catalyst.

6. The process as claimed in claim 1, wherein the olefin comprises 2 to 20 carbon atoms.

7. The process as claimed in claim 1, wherein the aromatic compound is selected from the group formed by benzene, naphthalene, anthracene, phenanthrene, and substituted derivatives thereof.

8. The process as claimed in claim 1, wherein the aromatic compound is benzene.

9. The process as claimed in claim 7, wherein the aromatic compound is selected from among alkylbenzene, hydroxybenzene, alkoxybenzene, alkylnaphthalene, hydroxynaphthalene, alkoxynaphthalene, alkylanthracene, hydroxyanthracene, alkoxyanthracene, alkylphenanthrene, hydroxyphenanthrene, and alkoxyphenanthrene.

10. The process as claimed in claim 1, wherein the alkylating agent is a polyalkylated aromatic compound, the aromatic compound is a non-alkylated aromatic compound, and wherein, during the alkylation, at least one alkyl group is transferred from the polyalkylated aromatic compound to the non-alkylated aromatic compound.

11. The process as claimed in claim 10, wherein the polyalkylated aromatic compound comprises an alkyl group having 2-20 carbon atoms.

12. The process as claimed in claim 10, wherein the polyalkylated aromatic compound comprises an alkyl group having 6-20 carbon atoms.

13. The process as claimed in claim 10, wherein the aromatic compound is selected from the group formed by benzene, naphthalene, anthracene, phenanthrene, and substituted derivatives thereof.

14. The process as claimed in claim 10, wherein the aromatic compound is selected from among alkylbenzene, hydroxybenzene, alkoxybenzene, alkylnaphthalene, hydroxynaphthalene, alkoxynaphthalene, alkylanthracene, hydroxyanthracene, alkoxyanthracene, alkylphenanthrene, hydroxyphenanthrene, and alkoxyphenanthrene.

15. The process as claimed in claim 10, wherein the polyalkylated aromatic compound is a polyisopropylbenzene and the non-alkylated aromatic compound is benzene.

16. The process as claimed in claim 1, wherein the porous crystalline material is subjected to cation exchange with cations selected from among H.sup.+, cations of rare earths, and cations of metals of Groups VIII, IIA, IIIA, IVA, VA, IB, IIB, IIIB, IVB, VB and VIIB of the Periodic Table of the Elements.

* * * * *